(12) United States Patent
Durand

(10) Patent No.: US 7,945,320 B2
(45) Date of Patent: May 17, 2011

(54) IONTOPHORETIC DRUG DELIVERY SYSTEM

(75) Inventor: Emma Amelia Durand, Jamestown, RI (US)

(73) Assignee: Isis Biopolymer, Inc., Warwick, RI (US)

( * ) Notice: Subject to any disclaimer, the term of this patent is extended or adjusted under 35 U.S.C. 154(b) by 0 days.

(21) Appl. No.: 12/192,540

(22) Filed: Aug. 15, 2008

(65) Prior Publication Data
US 2009/0048556 A1   Feb. 19, 2009

Related U.S. Application Data

(60) Provisional application No. 60/956,558, filed on Aug. 17, 2007.

(51) Int. Cl.
*A61N 1/30* (2006.01)
(52) U.S. Cl. ........................................ 604/20
(58) Field of Classification Search .................. 604/20, 604/501, 890.1
See application file for complete search history.

(56) References Cited

U.S. PATENT DOCUMENTS

| | | | |
|---|---|---|---|
| 4,708,127 A * | 11/1987 | Abdelghani | 601/2 |
| 4,919,648 A * | 4/1990 | Sibalis | 604/20 |
| 5,533,971 A * | 7/1996 | Phipps | 604/20 |
| 5,551,953 A | 9/1996 | Lattin | |
| 5,645,526 A | 7/1997 | Flower | |
| 5,797,867 A | 8/1998 | Guerrera | |
| 5,830,175 A | 11/1998 | Flower | |
| 5,895,369 A * | 4/1999 | Flower | 604/20 |
| 6,200,250 B1 * | 3/2001 | Janszen | 493/383 |
| 6,223,075 B1 * | 4/2001 | Beck et al. | 604/20 |
| 6,317,630 B1 | 11/2001 | Gross | |
| 6,597,946 B2 | 7/2003 | Avrahami | |
| 6,638,241 B2 | 10/2003 | Yerushalmy | |
| 6,708,050 B2 | 3/2004 | Carim | |
| 7,150,975 B2 | 12/2006 | Tamada | |
| 2002/0062102 A1 * | 5/2002 | Keusch et al. | 604/20 |
| 2003/0208152 A1 * | 11/2003 | Avrahami et al. | 604/20 |
| 2004/0131760 A1 | 7/2004 | Shakespeare | |
| 2004/0131897 A1 | 7/2004 | Jenson | |
| 2005/0101841 A9 | 5/2005 | Kaylor | |
| 2005/0182389 A1 | 8/2005 | LaPorte | |
| 2005/0226921 A1 | 10/2005 | Kortzebom | |
| 2005/0267440 A1 | 12/2005 | Herman | |
| 2006/0024358 A1 | 2/2006 | Santini | |
| 2006/0062838 A1 * | 3/2006 | DiPierro et al. | 424/449 |
| 2006/0173514 A1 | 8/2006 | Biel | |
| 2008/0154179 A1 | 6/2008 | Cantor et al. | |
| 2009/0118710 A1 | 5/2009 | Kortzeborn | |

OTHER PUBLICATIONS

International Preliminary Report of Patentability (Chapter II) for PCT International Application No. PCT/US2008/073292, mailed Oct. 6, 2009.

* cited by examiner

*Primary Examiner* — Theodore J Stigell
*Assistant Examiner* — Brandy C Scott
(74) *Attorney, Agent, or Firm* — Pillsbury Winthrop Shaw Pittman LLP

(57) ABSTRACT

The iontophoretic drug delivery system includes electrodes controlled by a microprocessor controller to drive charged molecules contained in a drug reservoir through the skin into the issues of a patient. The iontophoretic drug delivery system further includes an antenna connected to the programmable microprocessor. The antenna allows for the programming of the microprocessor and for the exchange of patient, drug, and treatment related information between the microprocessor and an external device. The iontophoretic drug delivery system is also provided with buttons to allow a patient to manually activate the drug delivery system. The iontophoretic drug delivery system is housed within a thin polyester film membrane.

26 Claims, 14 Drawing Sheets

CIRCUITRY, PRIMARY COMPONENT SIDE

CIRCUITRY, FOR ANTENNA REFERENCE

DIELECTRIC, PRIMARY COMPONENT SIDE

CIRCUITRY, SECONDARY ELECTRODE SIDE

ELECTRODES, SECONDARY SIDE

DIELECTRIC, SECONDARY ELECTRODE SIDE

THROUGH HOLE FILL

MEDICAL FOAM, SECONDARY ELECTRODE SIDE

DRUG RESERVOIRS, SECONDARY ELECTRODE SIDE

CONDUCTIVE EPOXY, PRIMARY COMPONENT SIDE

COMPONENT PLACEMENT, PRIMARY SIDE

ENCAPSULANT, PRIMARY COMPONENT SIDE

COMPLETE CIRCUIT, PRIMARY COMPONENT SIDE
(DIELECTRIC FILL NOT SHOWN)

ASIC:
PATCH PROGRAMING

BATTERY:
POWER SOURCE

SWITCHING REGULATOR AND ASSOCIATED COMPONENTS:
CHARGE PUMP CIRCUIT FOR INCREASED ELECTRICAL OUTPUT

MEDICAL FOAM ADHESIVE AND BARRIER MEMBRANE, SECONDARY ELECTRODE SIDE

THREE DRUG RESERVOIRS, SECONDARY ELECTRODE SIDE

SWITCH ACTIVATION OF PATCH, SIDE VIEW

IONTOPHORETIC DRUG DELIVERY SYSTEM

CROSS REFERENCE TO RELATED APPLICATIONS

This application claims the benefit of priority to provisional application 60/956,558, filed Aug. 17, 2007, the contents of which is incorporated by reference herein in its entirety.

FIELD OF THE INVENTION

The present invention relates to the field of devices and systems for delivering drugs to medicate a patient, and more particularly to an iontophoretic drug delivery system.

BACKGROUND OF TEE INVENTION

Iontophoresis is a drug delivery system. Iontophoresis is a non-invasive method of propelling charged molecules, normally medication or bioactive-agents, transdermally by repulsive electromotive force. By applying a low-level electrical current to a similarly charged drug solution, iontophoresis repels the drug ions through the skin to the underlying tissue. In contrast to passive transdermal patch drug delivery, iontophoresis is an active (electrically driven) method that allows the delivery of soluble ionic drugs that are not effectively absorbed through the skin.

An electrode drives charged molecules into the skin. Drug molecules with a positive charge are driven into the skin by an anode and those molecules with a negative charge are driven into the skin by a cathode.

There are a number of factors that influence iontophoretic transport including skin pH, drug concentration and characteristics, ionic competition, molecular size, current, voltage, time applied and skin resistance. Drugs typically permeate the skin via appendageal pores, including hair follicles and sweat glands.

Iontophoresis has numerous advantages over other drug delivery methods. The risk of infection is reduced because iontophoresis is non-invasive. Also, iontophoresis provides a relatively pain-free option for patients who are reluctant or unable to receive injections. For skin tissues, drug solutions may be delivered directly to the treatment site without the disadvantages of injections or orally administered drugs. Further, iontophoresis minimizes the potential for further tissue trauma that can occur with increased pressure from an injection.

SUMMARY OF THE INVENTION

An iontophoretic drug delivery system is disclosed. The iontophoretic drug delivery system includes electrodes controlled by a microprocessor controller to drive charged molecules through the skin into the tissues of a patient The iontophoretic drug delivery system further includes a wireless signal receiver connected to the microprocessor controller. The wireless signal receiver allows for the programming of the microprocessor and for the exchange of patient, drug, and treatment related information between the microprocessor and an external device. The microprocessor may be programmed through the wireless signal receiver with drug delivery schedule information, including frequency and dosage, for a particular patient and medication. A drug reservoir contains charged drug molecules that are driven into the skin by the electrodes. The operation of the electrodes, frequency, duration, and level of voltage applied, is controlled by the microprocessor. A battery provides power to the iontophoretic device.

The iontophoretic drug delivery system may be optionally housed within a thin polyester film membrane. The iontophoretic drug delivery system is configured in the shape of a generally flexible patch that adheres to the skin of a patient with an adhesive. In one embodiment, the edges of the flexible patch may be provided with a high tack adhesive to maintain the integrity of the skin-patch boundary. A lower tack adhesive is provided within the internal area of the flexible patch to make the purposeful removal of the patch from the use less painful. The drug reservoirs can be formed of a membrane or a gel pad in which charged drug particles are injected.

The iontophoretic drug delivery system may contain different various numbers of drug reservoirs depending upon the particular treatment. Where a single drug is being delivered, the system may contain a single drug reservoir adjacent one electrode. Where a treatment requires two drugs that have oppositely charged solutions, the system may include a reservoir adjacent each of the oppositely charged electrodes. Where multiple drugs having the same charge are used, they may be either mixed into a single drug reservoir or placed in multiple drug reservoirs each adjacent a respective electrode having the same electric charge.

The size of the electrodes may vary in different embodiments depending upon the strength of the electrical current needed to be produced in order to drive drug molecules of various sizes into a patient's skin.

In one exemplary embodiment, the electrodes and the microprocessor, battery and antenna are attached on opposite sides of a flexible sheet. The electrodes, microprocessor, battery and antenna are electrically connected utilizing conductive silver ink. Through holes formed in the flexible sheet electrically connect the electrodes to the microprocessor, battery and antenna. The microprocessor and battery are attached to the system using conductive cement.

In another embodiment, the system main contain various sensors to measure parameters such as patient skin temperature, moisture at the system/patient skin interface, or other patient or drug delivery related parameters.

Other objects, features and aspects of the invention will become apparent from the following detailed description, the accompanying drawings, and the appended claims.

BRIEF DESCRIPTION OF THE DRAWINGS

The novel features that are considered characteristic of the invention are set forth with particularity in the appended claims. The invention itself, however, both as to its structure and operation together with the additional objects and advantages thereof are best understood through the following description of the preferred embodiment of the present invention when read in conjunction with the accompanying drawings, wherein:

FIGS. 4-14 disclose a process of forming circuitry for an iontophoretic drug delivery system, wherein:

FIGS. 4 and 4A depict a printing of circuitry on a primary component side of a layer;

FIG. 5 depicts a deposition of dielectric material on a primary component side of a layer;

FIG. 6 depicts a printing of circuitry on a secondary component side of a layer;

FIG. 7 depicts formation of electrodes on a secondary component side of a layer;

FIG. 8 depicts a deposition of dielectric material on a secondary component side of a layer;

FIG. 9 depicts a filing of a through hole in a layer;

FIG. 10 depicts the attachment of laser cut foam to a secondary component side of a layer;

FIG. 11 depicts a formation of drug reservoirs on a secondary component side of a layer;

FIG. 12 depicts a deposition of a conductive epoxy on a primary component side of a layer;

FIG. 13 depicts a placement of components on a primary component side of a layer;

FIG. 14 depicts a deposition of an encapsulant on a primary component side of a layer;

DETAILED DESCRIPTION OF PREFERRED EMBODIMENTS

While the invention has been shown and described with reference to a particular embodiment thereof, it will be understood to those skilled in the art, that various changes in form and details may be made therein without departing from the spirit and scope of the invention.

Figure 1:
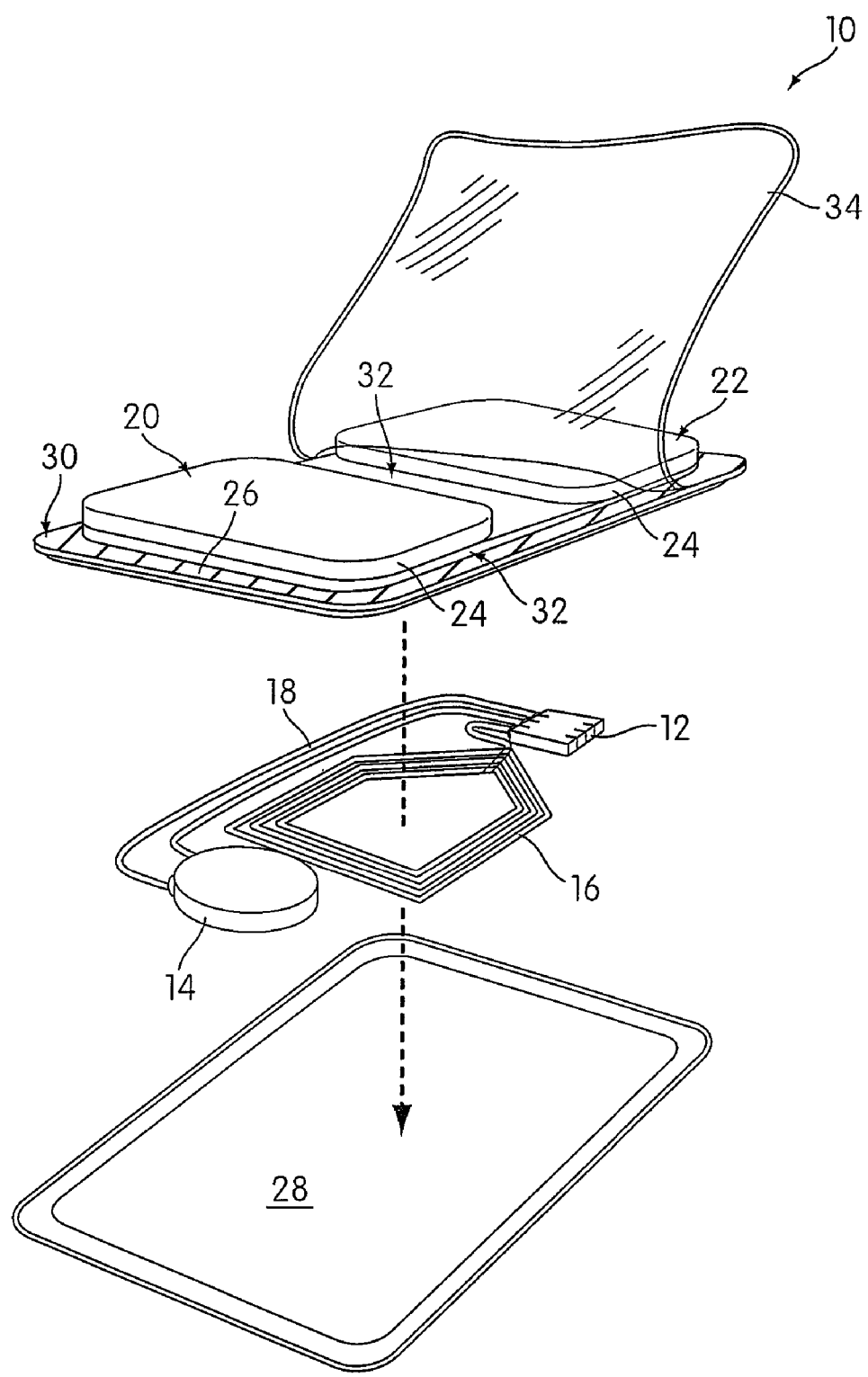
FIG. 1 discloses an exploded isometric view of a iontophoretic drug delivery system.

FIG. 1 discloses an exploded isometric view of an iontophoretic drug delivery system 10. System 10 provides a non-invasive method of propelling high concentrations of a charged substance, normally medication or bioactive-agents, transdermally by repulsive electromotive force. Iontophoretic drug delivery system 10 includes a microprocessor controller 12, a battery 14, an antenna 16, printed flexible wiring 18, an electrode 20, and an electrode 22. Drug reservoirs 24 are coupled to electrodes 20 and 22. Electrodes 20 and 22 and drug reservoirs 24 are contained in flexible layer 26 that conforms to the patient's body in the area of application. Layer 26 and layer 28 are bonded together to seal and protect microprocessor controller 12, battery 14, antenna 16, and printed flexible wiring 18. The construction and configuration shown is an example and not intended to be limiting.

Antenna 16 provides a wireless capability for system 10 to communicate with other external devices. In an exemplary embodiment, antenna 16 may be an RFID antenna, a bluetooth enabled device, an infra-red wireless device, or another wireless signal receiver. Antenna 16 may function as an RFID antenna or can receive signals from an outside device through capacitive coupling. Antenna 16 can also be configured in the shape of inductive coils in order to receive signals from an outside device through inductive coupling.

A high-tack adhesive 30 is placed on an outer edge of layer 26 and a low-tack adhesive 32 is placed within the internal area of the skin contacting surface of layer 26. High-tack adhesive 30 extends around the periphery of layer 26 and secures the outer edge of system 10 to the skin of a patient. High-tack adhesive 30 is used to prevent moisture or physical force from peeling system 10 off of the skin of a patient. Low-tack adhesive 32 is placed in the internal area of layer 26 (i.e. inward with respect to the high tack adhesive 30) to maintain contact between system 10 and the skin of the patient. The use of low-tack adhesive 32 makes removal of system 10 from the skin of a patient less painful, while the high tack adhesive 30 provides stronger bonding at the periphery where it is needed most to prevent lifting of the edge of system 10 or exposing system 10 to moisture. A preferred type of adhesive for high-tack adhesive 30 is a silicone based adhesive that is rapidly cured with an electron beam or UV radiation. Preferably, the adhesive is not present between the drug reservoir 24 and the skin, as this contact could alter the properties of adhesive 30 and/or influence the release of the drug. System 10 eliminates any interaction between the drug and adhesive matrix. In an exemplary embodiment, these adhesives may have peel strengths of 8.5 or 9.3 lbs/in. Adhesives with stronger or weaker peel strengths may be used with system 10.

A release layer 34 is placed over adhesive 30 and 32 to protect adhesive 30 and 32. Layer 34 is removed from system 10 just prior to bonding system 10 to the skin of a patient. Layer 34 makes sufficient contact with adhesive 30 and 32 to hold layer 34 to system 10 while allowing a user to easily peel layer 34 off of system 10. Typically, layer 34 is coated with a silicone based release coating to ensure that it can be peeled off without degrading adhesives 30 and 32.

Charged drug molecules are contained within drug reservoirs 24, which faces the patient's skin through an opening in layer 26. Drug reservoirs 24 may be a gel pad or membrane to which the charged drug molecules contained in a solution are applied or injected. By impregnating a gel pad or membrane with charged drug molecules, the charged drug molecules are not able to readily be absorbed into a patient's body without the operation of electrodes 20 and 22. In one embodiment, drug reservoirs 24 are a conductive medium to support the function of electrodes 20 and 22. By making drug reservoirs 24 also a conductive medium, system 10 can function with a lower amount of current, thereby extending battery 14 life and reducing the amount of current put into a patient's skin, of which a high amount of current can cause irritation. Typically, the solution is injected through a port into drug reservoirs 24. Electrodes 20 and 22 drive the charged drug molecules out of drug reservoirs 24 into the skin of a patient. Where the reservoir 24 includes a gel, the drug in ionic form may be mixed with the gel matrix cured together and assembled into the system 10.

The basis of ion transfer lies in the principle that like poles repels and unlike poles attract. Ions, being particles with a positive or a negative charge are repelled into the skin by an identical charge the electrode places over it. When a direct electric current activates electrodes 20 and 22, anions in the solution, ions with a negative charge, are repelled from the negatively charged electrode. Positively charged ions (cations) are likewise repelled from the positive electrode. The electrical current drives ions through the skin that would not be absorbed passively. The quantity of ions that are made to cross the skin barrier is proportional to the current density and to the amount of time the current flows through the solution. Current density is determined by the strength of electric field and the electrode size. A desired current strength is in the range of 0.4 mA or 2.0 mA per square inch of electrode 20 and 22 surface. This current strength is below sensory perception of a typical human patient. If electrodes 20 and 22 are too small, thereby concentrating the current (or if the current is too high), it may be more uncomfortable for the patient, as the current density may be sensed as an irritant.

Electrodes 20 and 22 and flexible printed wiring 18 are preferably made from a flexible material that can bend with layer 26 in conformity to the application area of the patient's body. One exemplary flexible material is silver conductive ink with resistivity of 8 to 10 milliohms per square. The resistivity of silver conductive irk within the range of 8 to 10 milliohms per square is desirable in order to have sufficient current to drive drugs into the stratum corneum. The ink may be silver (Ag), for example, and may be printed (e.g. by screen printing or gravure rolling) onto layer 26. Most commercially available silver conductive inks have a resistivity in the range of 14 to 18 milliohms per square, which limits the current available to drive the drugs through the stratum corneum. Electrodes 20 and 22 may be formed of silver chloride (AgCl).

System 10 includes two electrodes 20 and 22. In a particular drug treatment, the charged drug molecules will typically have one charge. Thus, only one of electrodes 20 or 22 can drive the charged drug molecules into the skin of the patient. The electrode that drives the charged drug molecules into the patient's skin is sometimes referred to as an active electrode, which is coupled with drug reservoir 24. A passive electrode that is not coupled to a drug reservoir 24 completes the circuit with the active electrode for creating a current for driving charged drug molecules into the patient's skin. In other drug treatments, the solutions containing charged drug molecules may have both positive and negative charges. In that example, both electrodes are active electrodes and both are coupled to a drug reservoir 24.

In many drug treatments, a single drug is used. However, it is common for the efficacy of many drugs to be increased by combining their delivery with other drugs. Thus, system 10 may be configured to deliver multiple types of charged drug molecules. In the case where the multiple drug molecules have the same charge, those drugs may be combined into a single solution and delivered from a single drug reservoir 24. In other embodiments where the multiple drugs have the same charge, but need to be delivered to the patient at different times or in different quantities, multiple electrodes 22 with multiple drug reservoirs 24 may be used. In a case where there are two drugs having molecules of opposite polarity, both electrodes 20 and 22 are provided with drug reservoirs 24 for delivering their respective drugs to the patient. In one embodiment, drug reservoirs 24 are formed of hydro-gel (i.e., a water-based gel). In another embodiment, drug reservoirs 24 are formed on a membrane. The size electrodes 20 and 22 will vary depending upon the size of the charged drug molecule that they are trying to repel into the patient's skin. Thus, in embodiments where multiple electrodes with multiple drug chambers 24 are used, the sizes of the electrodes and drug chambers may vary, One or both electrodes 20 and 22 are made of Ag/AgCl printable conductive ink coating. Electrodes 20 and 22 are covered by drug reservoirs 24, which may be formed from hydrogel that contains the charged drug molecules. Electrodes 20 and 22 are printed to the flexible printed wiring 18 with a highly conductive Polymer Thick Film (PTF) ink. In a preferred embodiment, a lead-free, silver loaded isotropic conductive cement is used that provides an electrical and mechanical connection having resistance to moisture and thermal shock.

Battery 14 powers system 10. It is desirable to make battery 14 as thin as possible, along with the rest of system 10, in order to enhance the ability of system 10 to adhere to a patient's skin with minimal disruption to the patient. Battery cells on the order of 0.7 mm thickness can generate up to 3.0 volts of electricity and multiple arrays can generate and control up to 9.0 volts of electricity. This amount of power allows for wireless programming and data acquisition with microprocessor controller 12 through antenna 16. The type and construction of the battery is not intended to be limiting.

Iontophoretic drug delivery system 10 may be used, in one exemplary embodiment, as a method of local drug delivery in a variety of clinical settings. System 10 can administer a local anesthetic to prevent painful sensations during skin puncture procedures, such as gaining venous access or injecting a drug intradernally or subcutaneously. System 10 can also deliver nonsteroidal anti-inflammatory drugs and corticosteroids inpatients with musculoskeletal inflammatory conditions.

The rate, timing and pattern of drug delivery using iontophoretic drug delivery system 10 is controlled with microprocessor controller 12 by varying the electrical current applied to electrodes 20 and 22. Microprocessor controller 12 can be programmed to provide a variety of drug delivery profiles where the duration and frequency of drug delivery is varied based upon the treatment parameters. The speed with which a drug delivery system can provide efficacious blood levels of the target drug determines the onset of therapeutic action. Iontophoretic drug delivery system 10 allows many drugs to pass directly through the skin into underlying issue and the bloodstream at a rate that is significantly more rapid than oral or passive transdermal drug delivery methods. Microprocessor controller 12 is programmed wirelessly through antenna 16. In one exemplary embodiment, microprocessor controller 12 to configured accept programming once and only once, thereby ensuring that system 10 could not be erroneously reprogrammed or purposefully misprogrammed by various electronic devices.

As an option, microprocessor controller 12 may also perform the function of data acquisition of drug delivery information on the actual drug delivery performed by system 10. Drug delivery information, for example, can include an electronic record of the date, time and quantity of each dose delivered; providing information for determining patient compliance. Electrodes 20 and 22 can be used to determine whether system 10 is in contact with the patient's skin by the operation of electrodes 20 and 22 and the resistivity of the patient's skin in the electrode-skin-electrode circuit formed when system 10 is in contact with the patient's skin.

Figure 20:
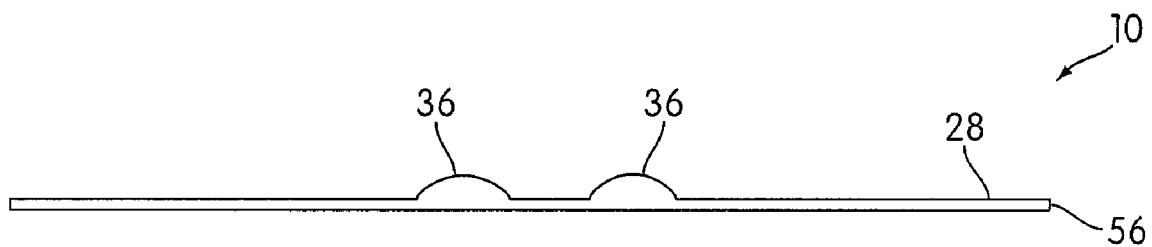
FIG. 20 illustrates a side view of a button for manually operating an iontophoretic drug delivery system.

As an option, system 10 also may include a manual button array 36 (shown in FIG. 20). Manual button array 36 is coupled to microprocessor controller 12. Manual button array 36 allows a patient to manually operate system 10. System 10 is preferably programmed with drug delivery information to automatically deliver drugs to the patient. A patient can deviate from or override this program and manually operate system 10 to deliver drugs with manual button array 36. Manual button array 36 can allow a patient to deviate from the drug delivery information and provide either longer or shorter drug dosages more or less often than instructed in the drug delivery information. A patient can also turn off system 10 with manual button array 36, for example when they are feeling negative side affects from the drug delivery.

Electrodes 20 and 22, flexible printed wiring 18, antenna 16 and other circuitry components in system 10, in a preferred embodiment, are made from Polymer Thick Film (PTF) flexible circuits that are manufactured using a technology that consists of a low-cost polyester dielectric substrate and screen-printed thick film conductive inks. These circuits are made with an additive process involving the high-speed screen printing of conductive ink. Multi-layer circuits are manufactured using dielectric materials as an insulating layer, and double-sided circuits using printed through-hole technologies. FIGS. 4-15 show an exemplary method of fabricating system 10. Both active and passive surface mount components can be adhered to PTF flexible circuit assemblies with Conductive Adhesives (CA's) or with Anisotropic Conductive Adhesives (ACA's). In a preferred embodiment, to ensure optimal performance when system 10 is flexed, all components are encapsulated between layers 26 and 28, which are bonded together using a hydrophobic UV-cured material developed specifically for medical applications.

It is advantageous to utilize PTF flexible circuits because they are inherently less costly than for example copper based circuits. PTF are formed on a dielectric substrate that circuit traces are printed directly upon. In addition, PTF typically uses a PET substrate which is significantly less expensive than the polyimide substrate which is commonly used in copper circuitry. In addition, as PTF circuits are more environmentally friendly as they are printed directly and do not require the removal of materials where chemicals are used to selectively etch away the copper foil to leave behind a conductive pattern.

The charged drug molecules vary in size for different drug compounds. Larger drug molecules require stronger electromagnetic forces to drive them into the skin of a patient. Smaller drug molecules require lesser electromagnetic forces to drive them into the skin of a patient. Thus, it is desirable to vary the size of electrodes 20 and 22 based upon the size of the drug compounds in order to deliver an optimal amount of electromagnetic force to drive the drug molecules into the patient's skin. System 10 is therefore preferably manufactured for a specific drug molecule size by having a tailored size for each electrode 20 and 22.

The table shown below provides an exemplary list of drugs, the charge of the drug molecules and solution, and the purpose/condition for which the drugs are used.

| Drug | Charge of Solution/Drug Molecules | Purpose/Condition |
| --- | --- | --- |
| Acetic acid | − | Calcium deposits |
| Atropine sulphate | + | Hyperhidrosis |
| Calcium | + | Myopathy, myospasm |
| Chloride | − | Sclerolytic, scar tissue |
| Citrate | − | Rheumatoid arthritis |
| Copper | + | Astringent |
| Dexamethasone | − | Tendinitis, bursitis |
| Glycopyrronium bromide | + | Hyperhidrosis |
| Iodine | − | Sclerolytic, scar tissue |
| Lidocaine | + | Dermal anesthesia |
| Magnesium | + | Muscle relaxant |
| Penicillin | − | Infected burn wounds |
| Poldine methyl sulfate | − | Hyperhidrosis |
| Potassium iodide | − | Scar Tissue |
| Salicylate | − | Analgesic, plantar warts |
| Sodium chloride | − | Scar tissue |
| Silver | + | Chronic osteomyelitis |
| Zinc | + | Antiseptic, wound healing |

In various embodiments, the flux of charged drug molecules from drug reservoirs 24 into the patient's skin can be increased through the use of a skin permeation enhancer. A permeation enhancer is any chemical or compound that, when used in conjunction with the charged drug molecule, increases the flux of charged drug molecules from drug reservoir 24 into the skin of the patient. That is, skin permeation enhancers is a substance that enhances the ability of the charged drug molecule transfer from the drug reservoir and permeate into the patient's skin.

Such use of a permeation enhancers is advantageous because it reduces the amount of electrical power required to transfer the drug from a reservoir 24 and into the patient's skin. This means that less current can be used, which in turn reduces the potential for skin irritation. And it also means less power is drawn, meaning the battery can be made smaller and/or last longer.

The enhancer may be an excipient, i.e., a medicinally inactive agent, included in the reservoir 24 with the charged drug molecule. Preferably, where a gel is used in the reservoir to carry the drug, the permeation enhancer and the drug are soluble in the gel but not chemically bonded to the gel network, thus enabling them to more easily transfer from the gel to the skin. In some embodiments, the enhancer may be a molecule with a charge similar to the associated drug molecule.

For example, oleic acid has an synergistic effect on the ability of iontophoresis to promote skin permeation of insulin. The use of propylene glycol further increased this effect. One exemplary incipient that can enhance the flux of charged drug molecules from system 10 into a patient by means of iontophoresis is a fatty acid having from 1-9 carbon atoms. Preferably, the incipient contains at least one $C_2$-$C_6$ fatty acid. By means of an example, the fatty acid may be selected from the group of propionic acid, valeric acid, 2-methylbutanoic acid, 3-methylbutanoic acid, and combinations thereof. In one example, the fatty acid is a mixture of propionic acid and valeric acid.

The permeation enhancer need not be in the reservoir 24 with the drug, and could be applied to the skin contacting surface of the reservoir 24. This could help create an interface between the reservoir 24 and the skin for enhancing permeation of the drug.

Figure 2:
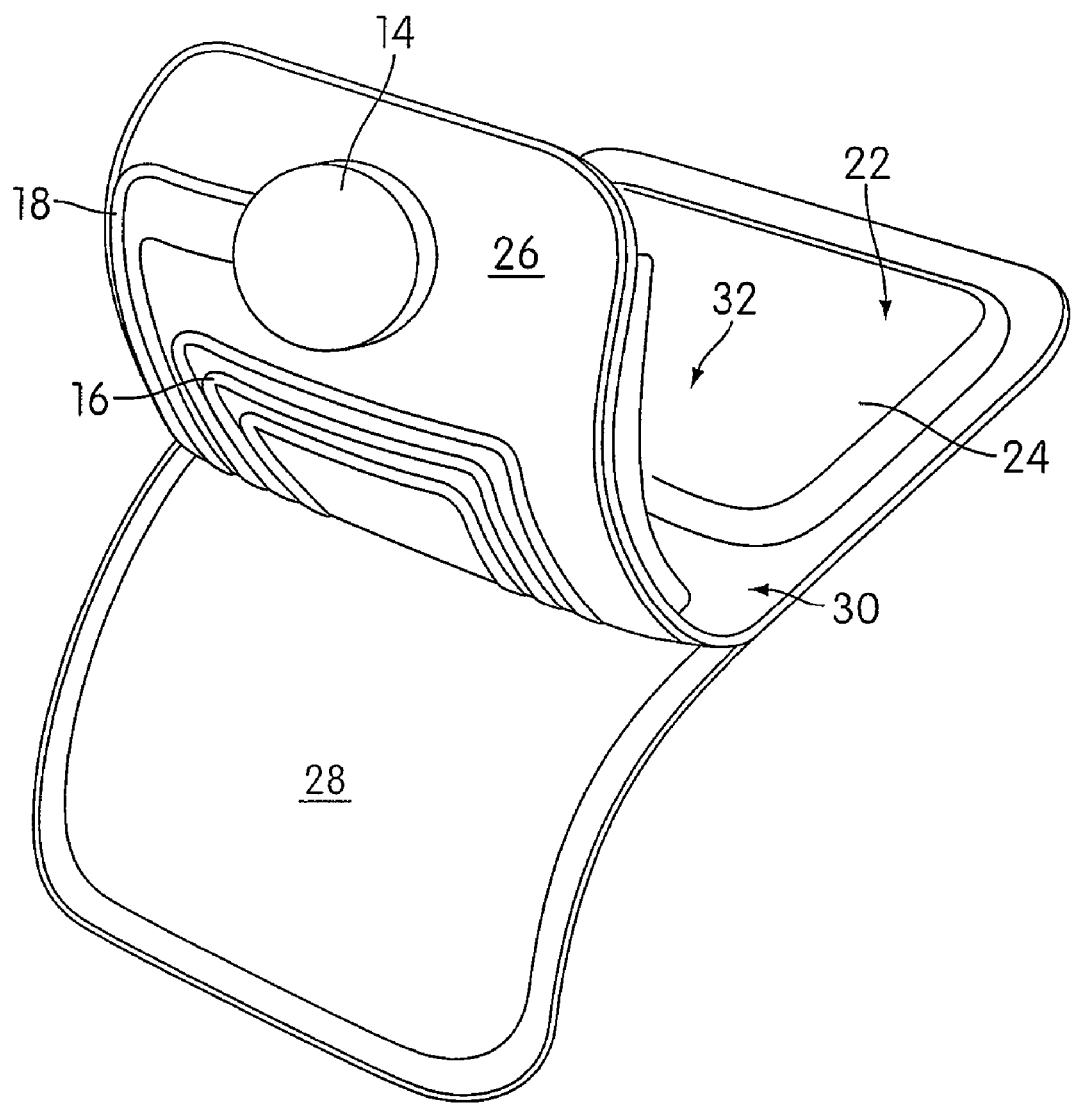
FIG. 2 discloses an isometric view of an iontophoretic drug delivery system.

FIG. 2 discloses an isometric view of an iontophoretic drug delivery system 10. Battery 14, antenna 16, and flexible printed wiring 18 are shown adhered to layer 26 with layer 28 partially pealed away. FIG. 2 demonstrates the flexibility of system 10 that enables system 10 to conform to the contours of a patient's body and be able to deform during normal activity and movement of the patient's body. In addition, this figure shows how system 10, when assembled, is a thin patch that intrudes minimally upon the patient's daily functions.

Figure 3:
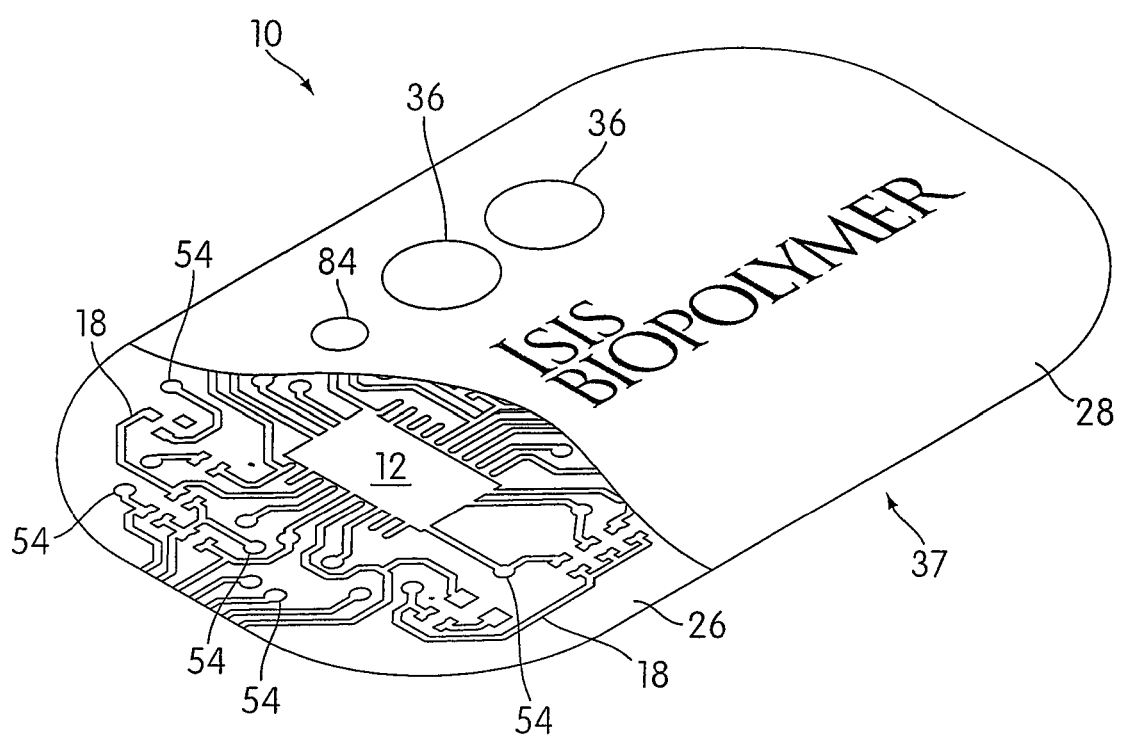
FIG. 3 discloses an isometric see-through view of an iontophoretic drug delivery system.

FIG. 3 discloses an isometric see-through view of an iontophoretic drug delivery system 10. Microprocessor controller 12, battery 14, antenna 16, printed flexible wiring 18, electrodes 20 and 22, and drug reservoirs 24 are shown sandwiched between layers 26 and 28. Manual button array 36 allows a patient to manually operate system 10. An indicator light 84 provides a visual indication of the status of system 10. Indicator light 84 is preferably a multi-colored LED, which may for example show green when operating normally, flash orange in a low power state, or flash red when a system failure occurs, as a non-limiting example. System 10 can include a variety of sensors 37 to monitor various parameters in the patient/system 10 environment. These parameters can include, by means of a non-limiting example, moisture, temperature, system 10/patient physical contact, and various patient parameters such as skin temperature, heart rate, etc. Information from sensors 37 can be used to provide positive feedback to system 10. For instance, if sensors 37 detect moisture at the system 10/patient skin interface, that may indicate that the patient is sweating. With this information, system 10 may be programmed to either increase the voltage delivered to electrodes 20 and 22 to drive the charged drug molecules through the added layer of sweat. Alternatively, system 10 may be programmed to stop delivery of the charged drug molecules until after the patient stops sweating and the sweat has evaporated.

Figure 4:
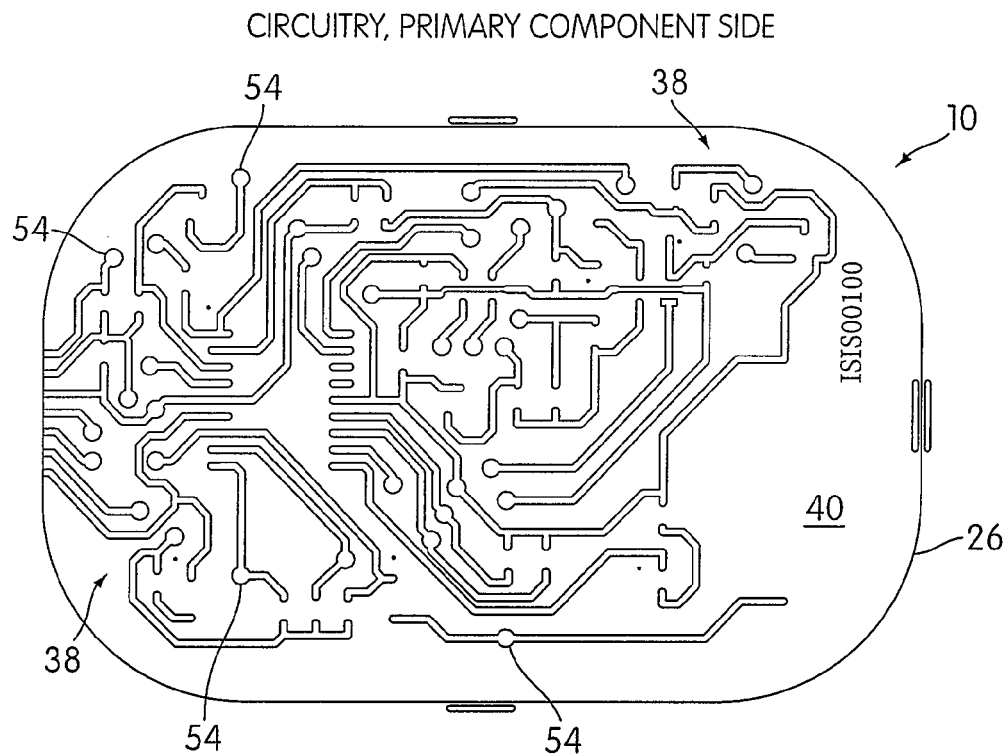
Figure 4A:
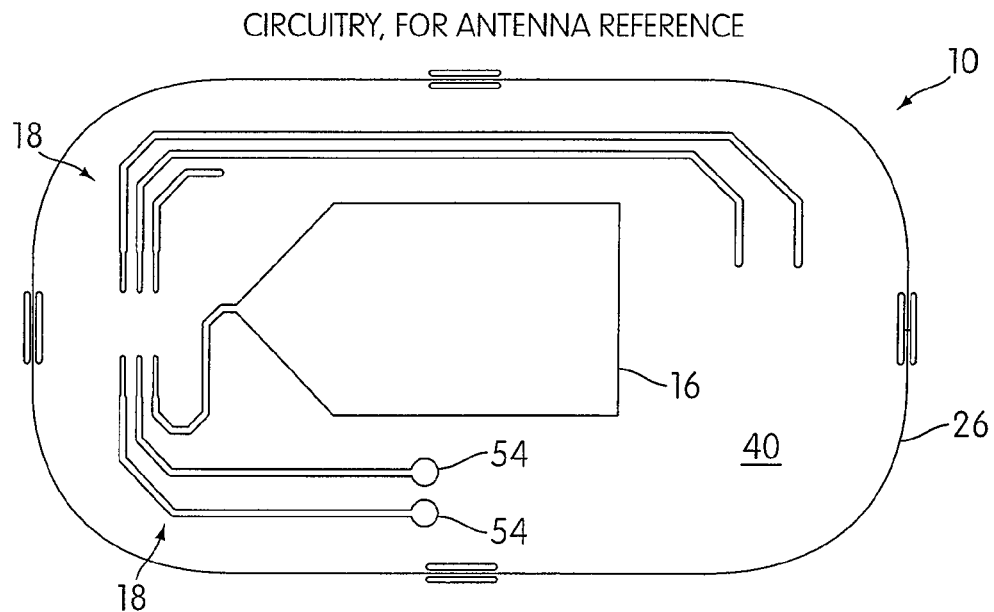

FIGS. 4-14 disclose a process of forming circuitry for an iontophoretic drug delivery system 10. FIG. 4 depicts a printing of circuitry 38 on a primary component side 40 of layer 26. Layer 26 is preferably made of a thin flexible film, such as polyethylene terephthalate (PET). Circuitry 38 is made of conductive silver ink that is printed onto layer 26. In FIG. 4A, antenna 16 is printed along with wirings 18 that interconnect antenna 16, battery 14, and microprocessor controller 12.

Figure 5:
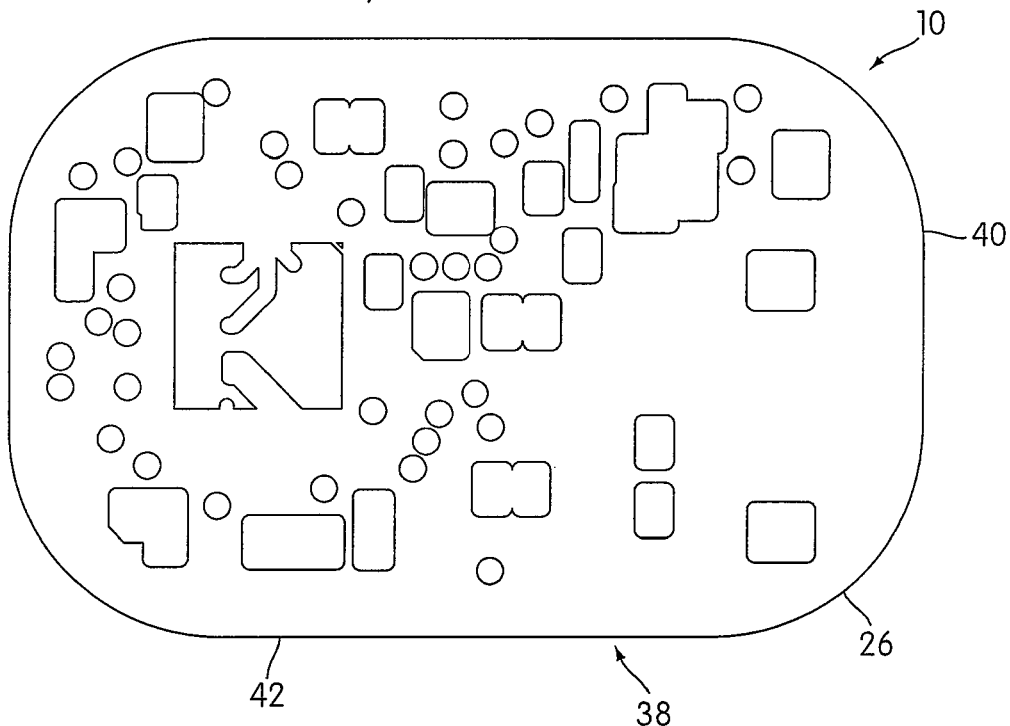

FIG. 5 depicts a deposition of dielectric material 42 on primary component side 40 of layer 26. Dielectric material 42 covers wirings 18 that interconnect antenna 16, battery 14, and microprocessor controller 12. Dielectric material 42 does not cover antenna 16. At this step, through holes 54 are formed by laser cutting layer 26. The dielectric material is printed on to layer 26. The dielectric is printed using a magnesium silicate pigment that is bound with urethane acrylate.

Figure 6:
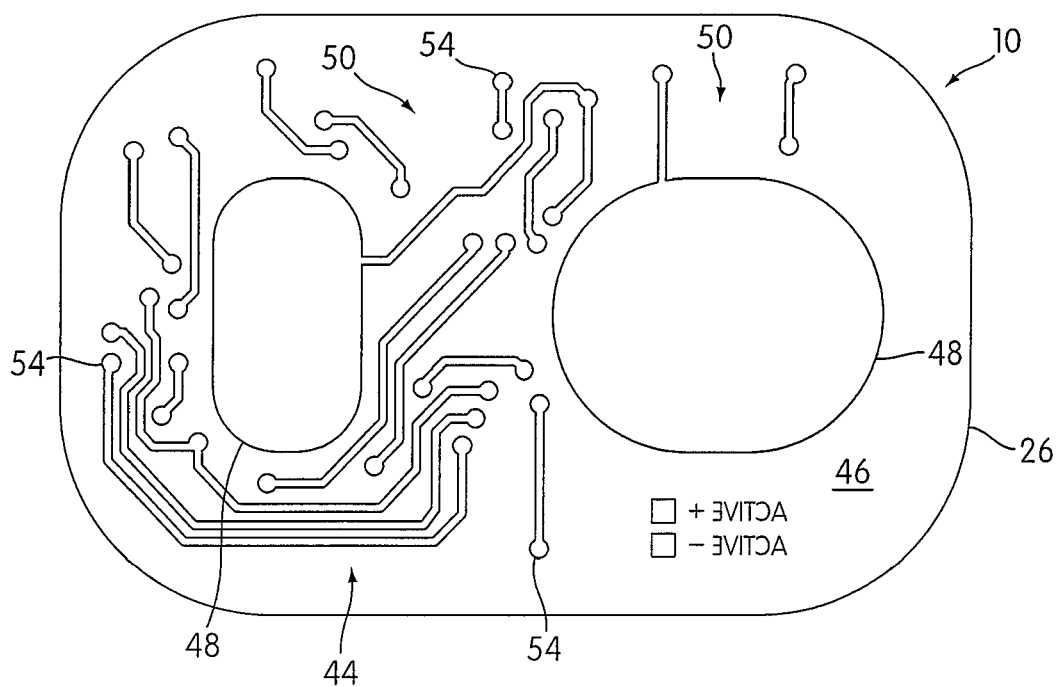

FIG. 6 depicts a printing of circuitry 44 on a secondary component side 46 of layer 26. Circuit 44 includes wirings 48 for electrodes 20 and 22 and wirings 50 for connecting electrodes 20 and 22 to battery 14 and microprocessor controller 12. Circuitry 44 is made of conductive silver ink that is printed onto layer 26. Secondary component side 46 makes contact with a patient's skin.

Figure 7:
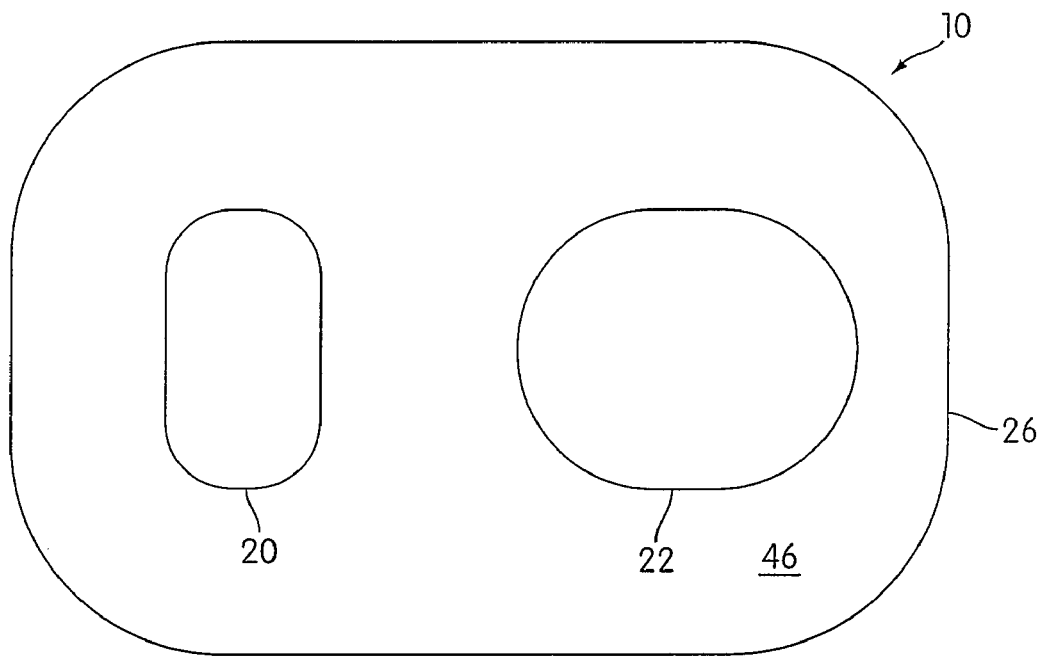

FIG. 7 depicts a formation of electrodes 20 and 22 on secondary component side 46 of layer 26. Electrodes 20 and 22 are formed on top of wirings 48. Electrodes 20 and 22 are formed of silver or silver chloride. In a preferred embodiment, wirings 48 have a higher resistivity than electrodes 20 and 22. Electrodes 20 and 22 may be made from a material having a resistivity lower than wirings 48 in order to deliver a desirable amount of electricity to a patient's skin that is just below a patient's sensory perception. Thus, in addition to varying electrode size to alter the amount of electricity delivered by electrodes 20 and 22 to accommodate drug molecules of varying sizes, the materials used to form electrodes 20 and 22 may also be varied to affect these parameters as well.

The larger of the two electrodes 22 would contain the positivity or negatively charged drug molecule. The smaller of the two electrodes 20 would be the return and would contain only the hydrogel material. For positively charged drug molecules, the larger electrode 22 is constructed of silver ink with one or multiple print passes as well as varied silver loading. The return electrode 20 is constructed of silver/silver chloride ink with one or multiple print passes as well as varied silver chloride loading. For a negatively charged drug molecules, the larger electrode 22 is constructed of silver/silver chloride ink with one or multiple print passes as well as varied silver chloride loading. The return electrode 20 is constructed of silver ink with one or multiple print passes as well as varied silver loading.

This combination of material and material sets enhances the drug delivery performance, stabilizes the pH and increases the delivery time of the patch system.

Figure 8:
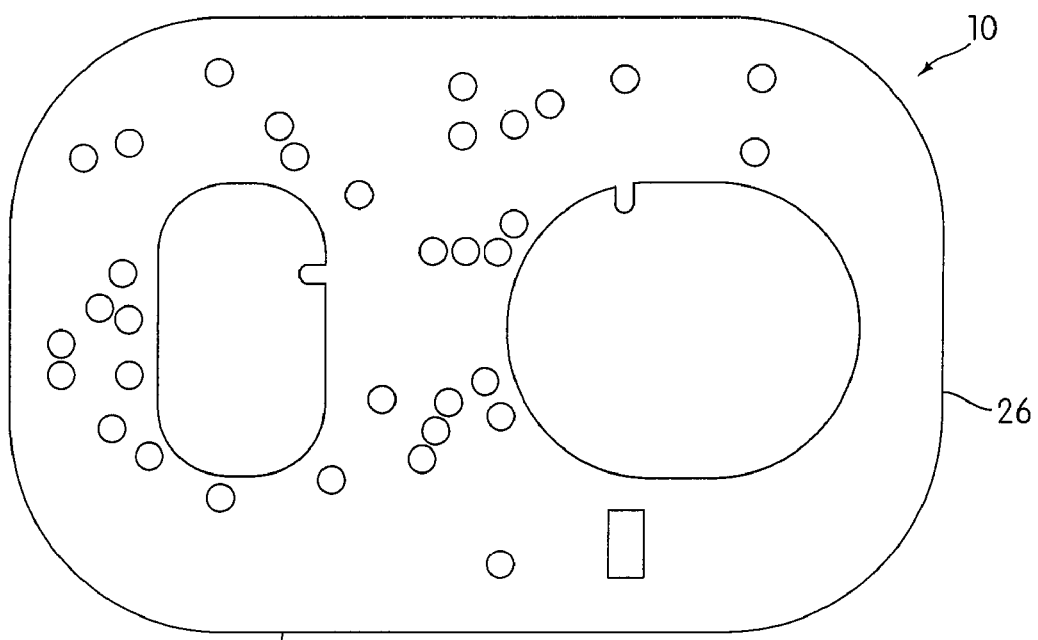

FIG. 8 depicts a deposition of dielectric material 52 on secondary component side 46 of layer 26. Dielectric material 52 is deposited to cover wirings 50. The dielectric material is not deposited on electrodes 20 or 22.

Figure 9:
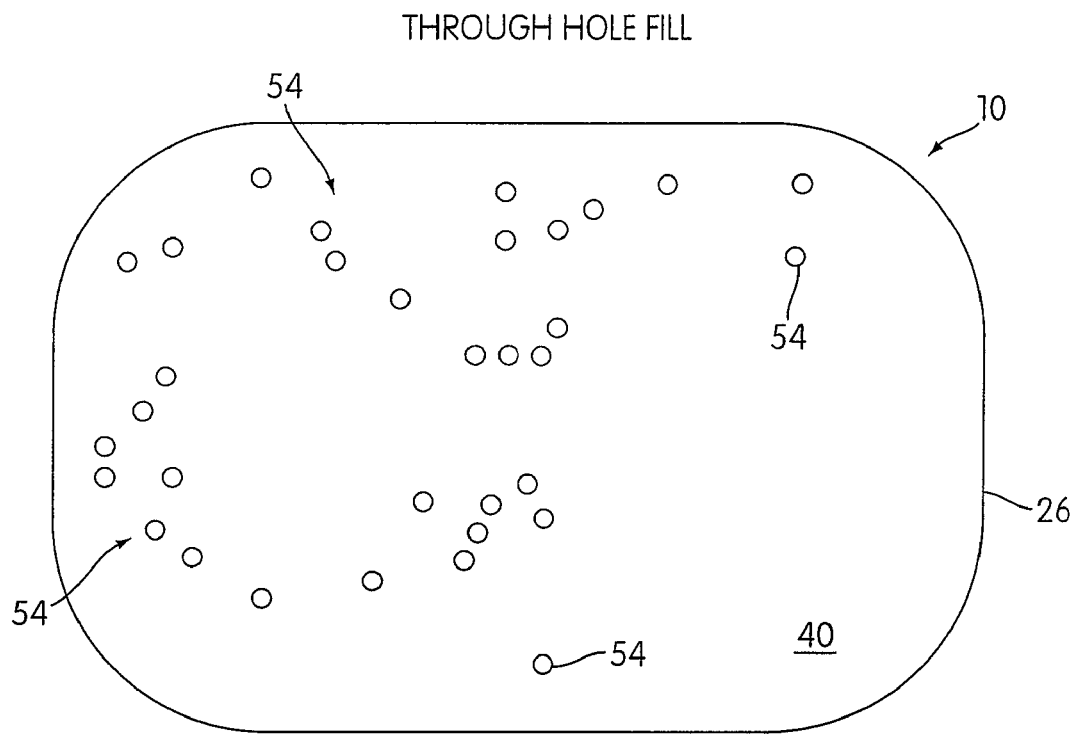

FIG. 9 depicts a filing of through holes 54 in layer 26. Through holes 54 are filled with a conductive material in order to electrically couple wirings 50 to circuitry 38. This conductive material is preferably printed silver ink.

Figure 10:
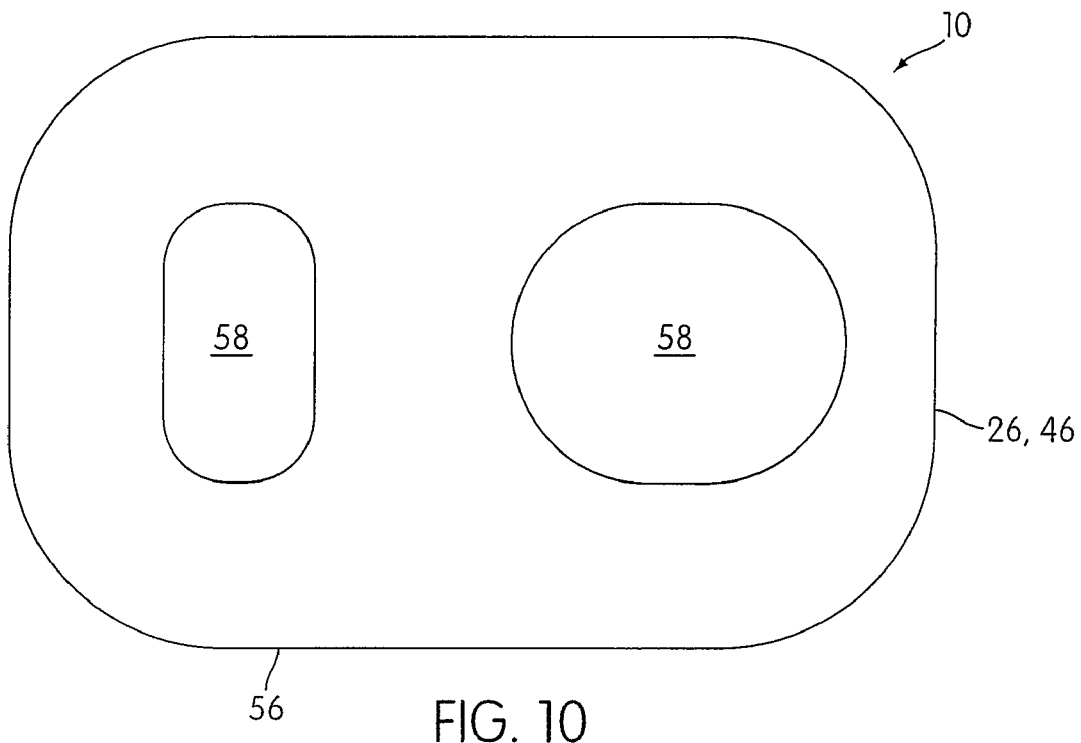

FIG. 10 depicts the attachment of laser or die cut foam 56 to secondary component side 46 of layer 26. Foam 56 is cut to have openings 58. Openings 58 are provided for the formation of drug reservoirs 24. Openings 58 coincide with the position of electrodes 20 and 22 on top of which drug reservoirs 24 are formed. Foam 56 is attached to secondary component side 46 of layer 26. In another embodiment, printed silicone adhesive is used in place of foam 56.

Figure 11:
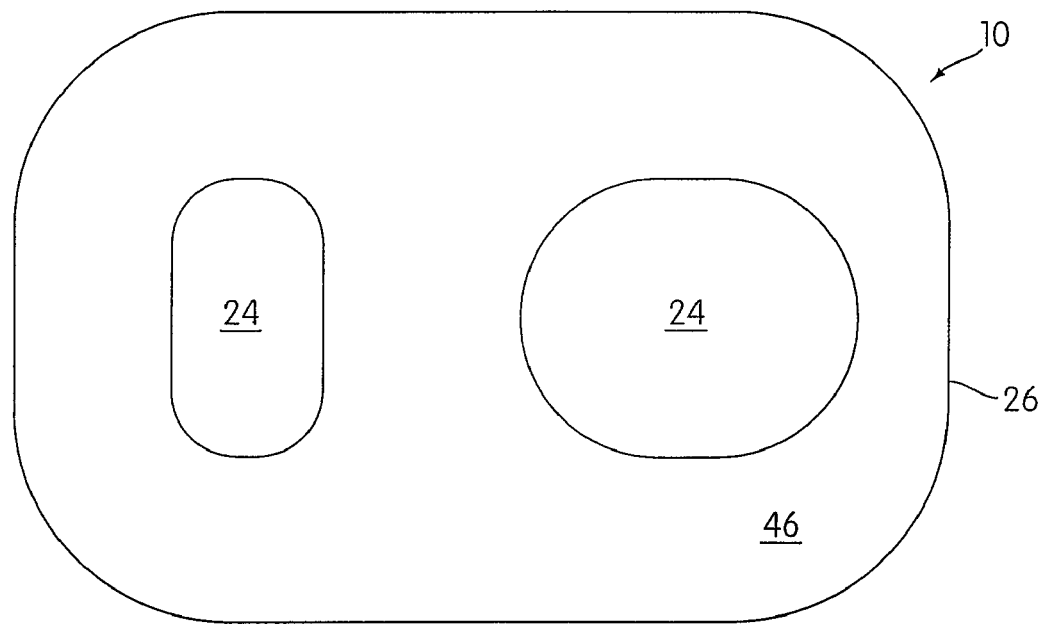

FIG. 11 depicts a formation of drug reservoirs 24 on secondary component side 46 of layer 26. In this exemplary embodiment, drug reservoirs 24 are formed from hydro-gel that is deposited within openings 58 of foam 56 over electrodes 20 and 22.

Figure 12:
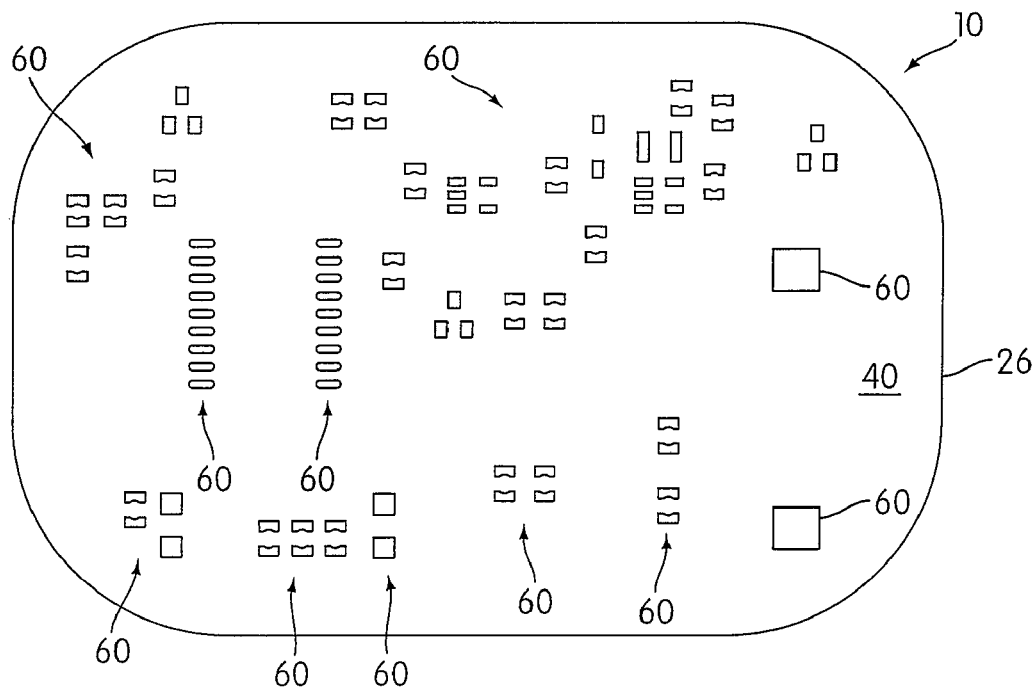

FIG. 12 depicts a deposition of conductive epoxy 60 on primary component side 40 of layer 26. Conductive epoxy 60 is deposited in the pattern shown in FIG. 12 to secure microprocessor controller 12 and battery 14 onto layer 26 and place those components into electrical connection with circuitry 38.

Figure 13:
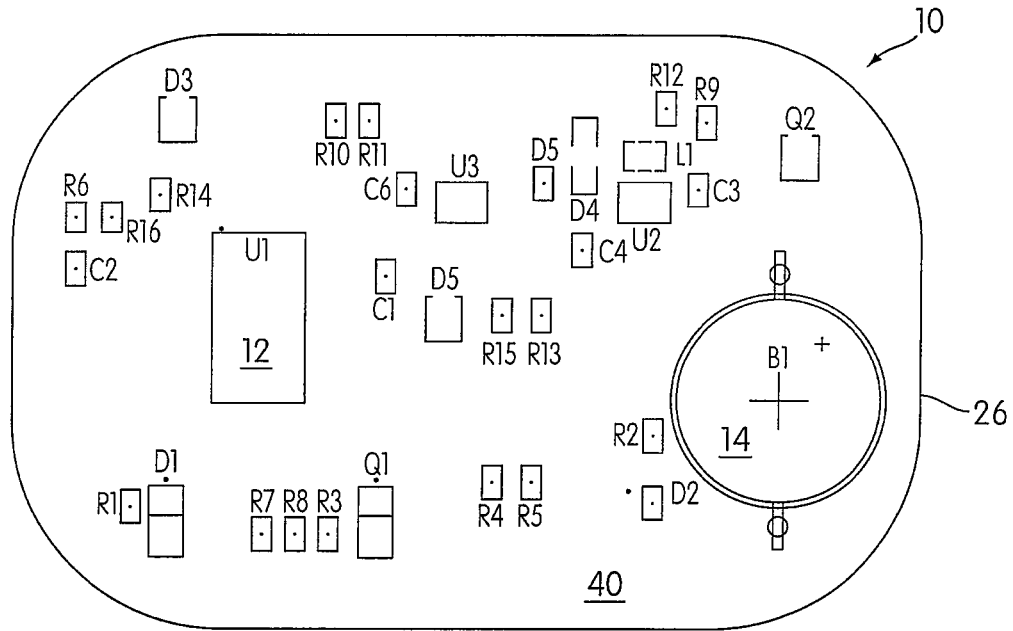

FIG. 13 depicts a placement of components 12 and 14 on primary component side 40 of layer 26. Microprocessor 12 and battery 14 are attached to layer 26 over the positions where conductive epoxy 60 (shown in FIG. 12) was deposited. The components labeled with the label "D" are diodes, the components labeled with "C" are capacitors, and the components labeled with "R" are resistors.

Figure 14:
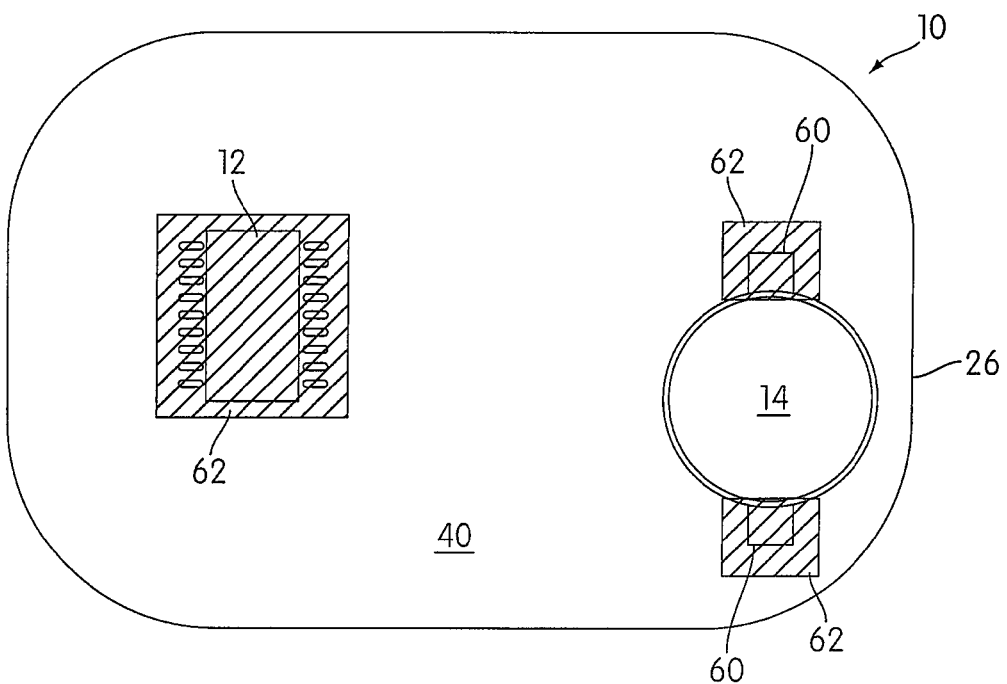

FIG. 14 depicts a deposition of an encapsulant material 62 on primary component side 40 of layer 26. Encapsulant material 62 covers the electrical connections that microprocessor 12 and battery 14 form with circuitry 38. Encapsulant material 62 is used to protect the electrical connections that microprocessor 12 and battery 14 form with circuitry 38 from damage from moisture or other contaminants. Encapsulant material 62, in one exemplary embodiment, is a Ultra-Violet (UV) curable encapsulation photopolymer designed to secure low profile surface mount devices to a flexible substrate.

Figure 15:
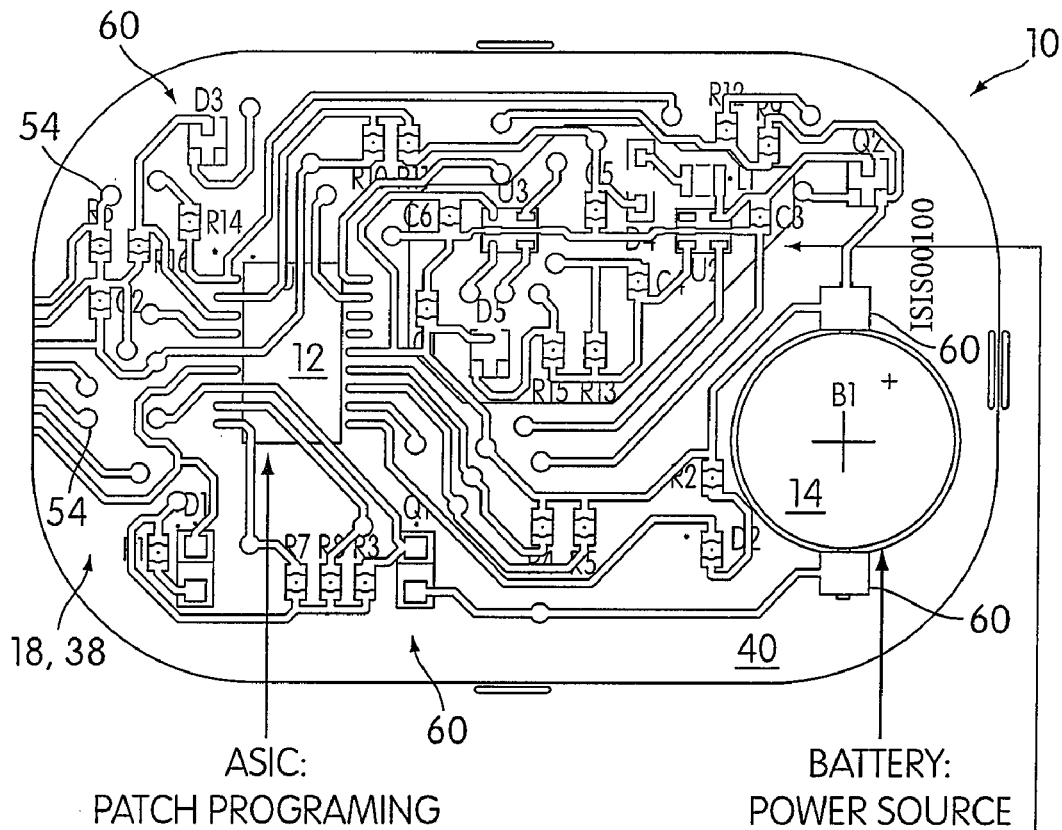
FIG. 15 illustrates a completed primary component side of a layer.
Figure 15:
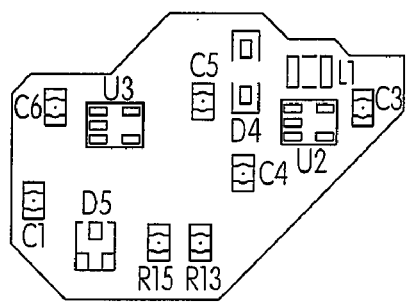

FIG. 15 illustrates a completed primary component side 40 of layer 26. Microprocessor controller 12 and battery are mounted to layer 26. Antenna 16 is formed and connected to microprocessor controller 12 with wirings 18. Through holes 54 interconnect microcontroller 12 and battery 14 to electrodes 20 and 22 on the secondary component side 46 of layer 26. Circuitry 38 includes a switching regulator and associated components as well as a charge pump for increased electrical output.

Figure 16:
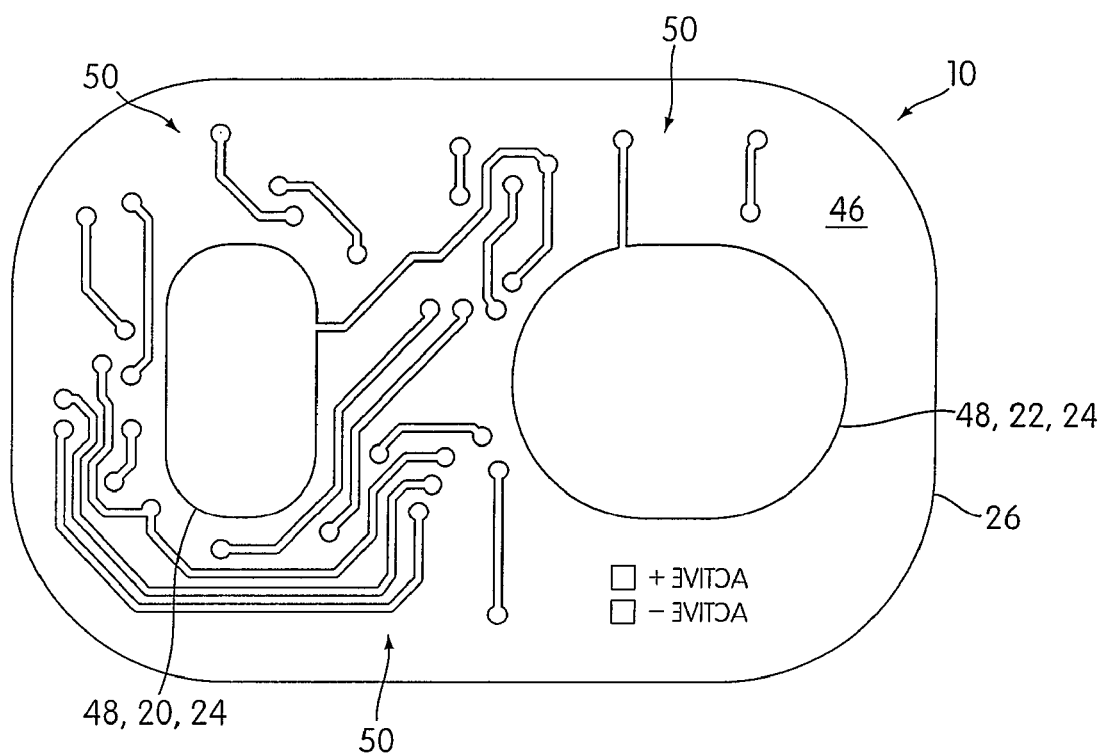
FIG. 16 illustrates a completed secondary component side of a layer.

FIG. 16 illustrates a completed secondary component side 46 of layer 26. Drug reservoirs 24 are formed over electrodes 20 and 22 and are surrounded by foam tape 56. The outer edges of secondary component side 46 are covered with high-tack adhesive 30. The central portion of secondary component side 46 is covered with low-tack adhesive. Wirings 50 connect electrodes 20 and 22 to battery 14 and microprocessor controller 12 by through holes 54.

Figure 17:
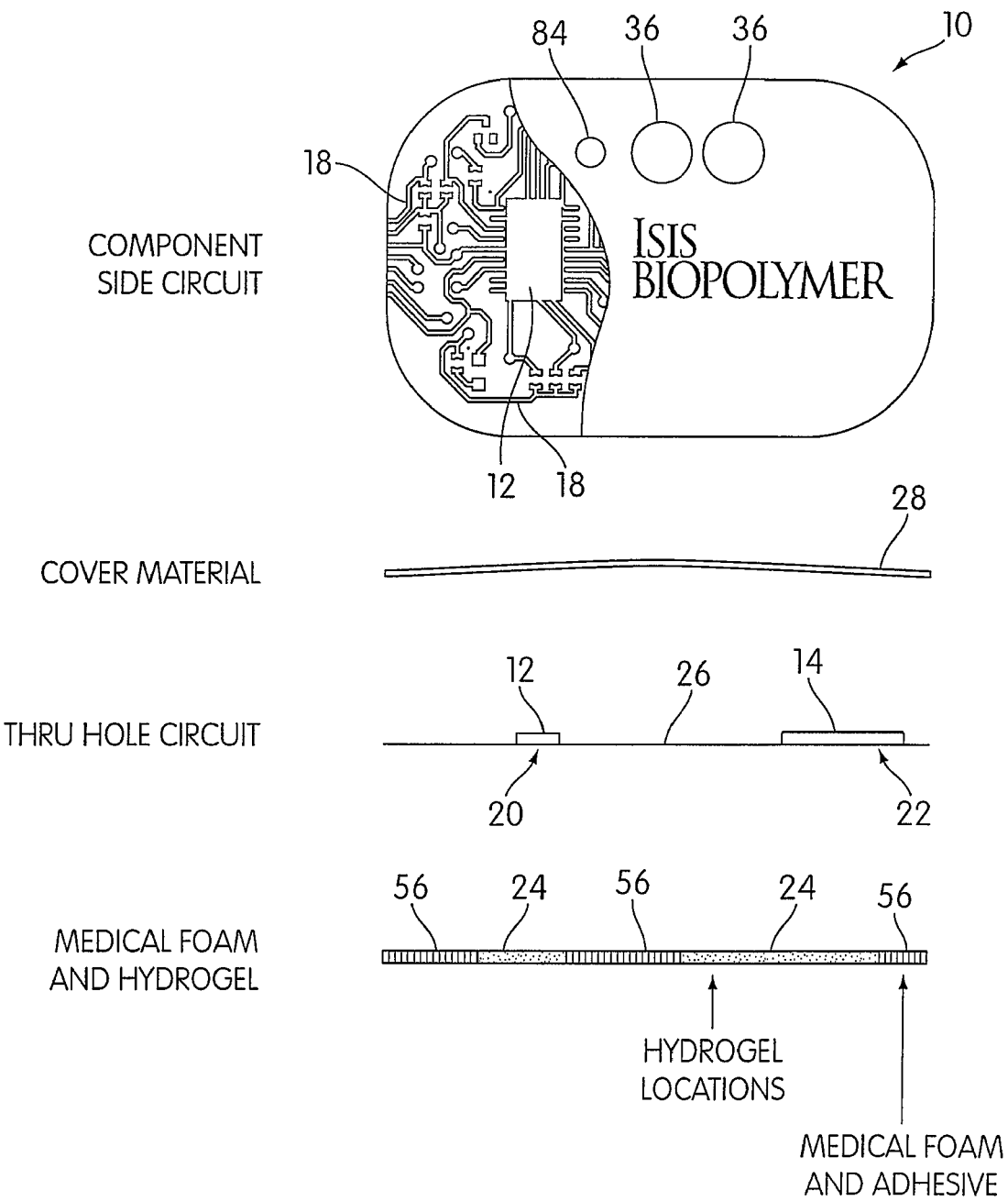
FIG. 17 illustrates a side view of an iontophoretic drug delivery system.

FIG. 17 illustrates a side view of iontophoretic drug delivery system 10. Layer 28 is shown covering microprocessor controller 12, battery 14, and antenna 16. Microprocessor controller 12, battery 14 and antenna 16 are attached to primary component side 40 of layer 26. On the secondary component side 46 of layer 26, electrodes 20 and 22 are printed on layer 26. Layer 26 is attached to foam layer 56, in which drug chambers 24 are formed. Adhesives 30 and 32 are placed on the bottom surface of layer 56 (as shown in FIG. 18).

Figure 18:
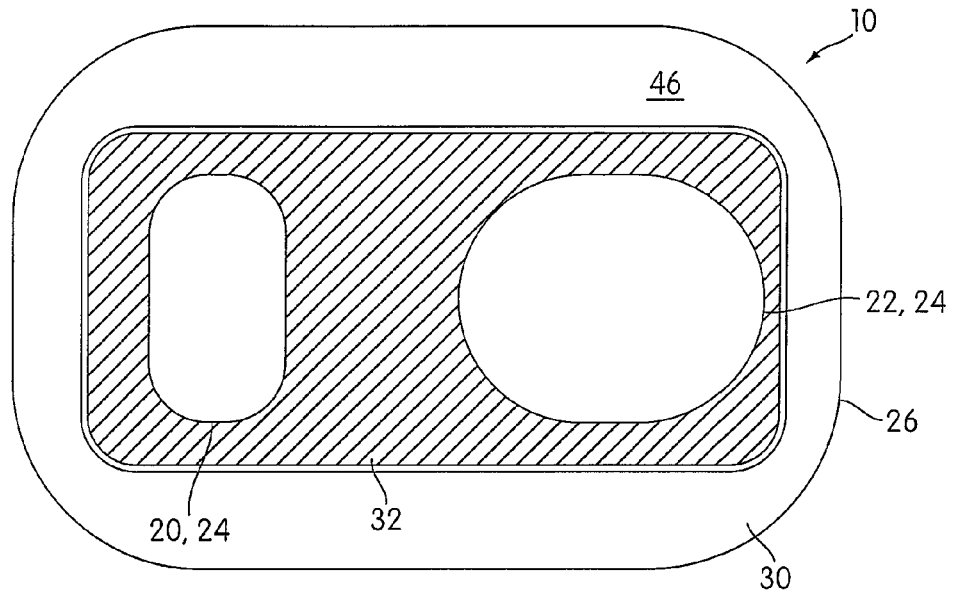
FIG. 18 illustrates an adhesive pattern on a secondary component side of a layer.

FIG. 18 illustrates an adhesive pattern on secondary component side 46 of layer 26. The peripheral portion of secondary component side 46 is covered with high tack adhesive 30. The dashed inner portion of secondary component side 46 is covered with low tack adhesive 32. Electrodes 20 and 22 and drug chambers 24 are not covered with any adhesive so that the adhesive does not interfere with the transference of charged drug molecules from drug chambers 24 into the patient's skin.

Figure 19:
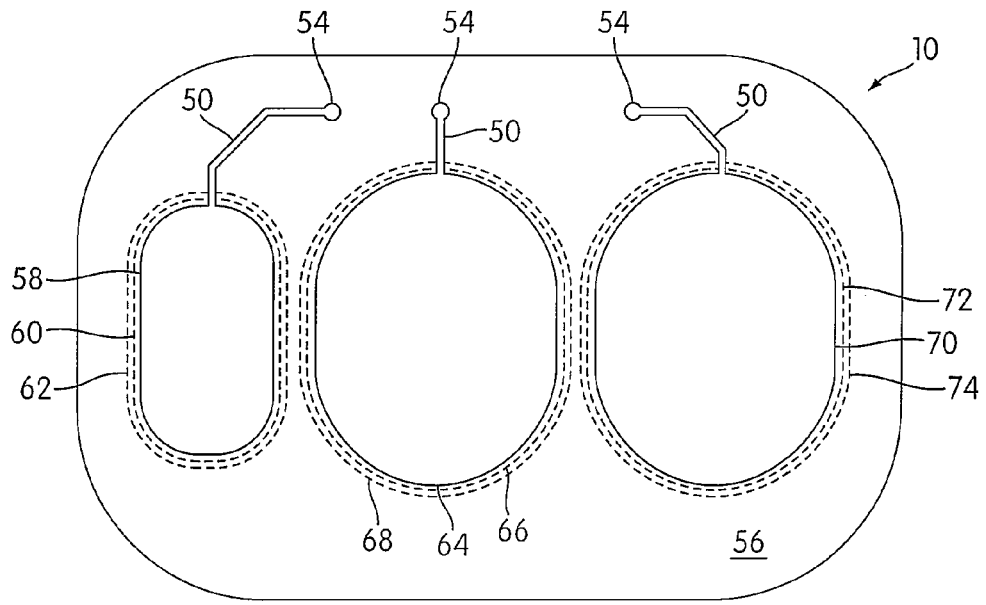
FIG. 19 illustrates an iontophoretic drug delivery system having three drug reservoirs.

FIG. 19 illustrates an alternative embodiment for iontophoretic drug delivery system 10. System 10 includes a first drug reservoir 58 formed on an electrode 60, which is formed on printed circuit 62. System 10 includes a second drug reservoir 64 formed on an electrode 66, which is formed on printed circuit 68. System 10 also includes a third drug reservoir 70 formed on electrode 72, which is formed on printed circuit 74. Printed circuits 62, 68 and 74 are connected with printed wirings 50 that lead to through holes 54. Electrodes 60, 66, and 70 are coupled to separate terminals of microprocessor controller 12 and are operated independently of each other by microprocessor controller 12. Electrodes 60, 66 and 70 are varied in size according to the variance in size of the charged drug molecules that electrodes 60, 66 and 70 drive into a patient's skin.

FIG. 20 illustrates a side view of a manual button array 36 for manually operating an iontophoretic drug delivery system 10. Manual button array, in this exemplary non-limiting embodiment, is formed of one or more poly-dome switch assemblies 36. Poly-dome switch assemblies 36.

While the invention has been shown and described with reference to a particular embodiment thereof, it will be understood to those skilled in the art, that various changes in form and details may be made therein without departing from the spirit and scope of the invention.

What is claimed is:

1. An iontophoretic drug delivery system for driving charged drug molecules into a tissue, comprising:
   a flexible body configured to conform to a portion of a patient's body that includes the tissue, the flexible body including a top surface, a bottom surface, and at least one through hole;
   a drug reservoir holding the charged drug molecules;
   an iontophoretic electrode configured to iontophoretically deliver the charged drug molecules from the drug reservoir into the tissue, the electrode being formed of an electroconductive material printed on the bottom surface of the flexible body, wherein the drug reservoir is located adjacent to the iontophoretic electrode such that the iontophoretic electrode is between the drug reservoir and the flexible body;
   a microprocessor controller configured to control iontophoretic delivery of the charged drug molecules from the drug reservoir into the tissue by the iontophoretic electrode, the microprocessor located adjacent to the top surface of the flexible body;
   circuitry that couples the microprocessor to the iontophoretic electrode, the circuitry being formed of flexible electroconductive material printed on the top surface of the flexible body;
   an electroconductive material in the at least one through hole that couples the circuitry to the iontophoretic electrode, wherein the electroconductive material fills the through hole such that moisture is prevented from passing from the bottom surface to the top surface via the through hole when at least a portion of the bottom surface is located adjacent to the tissue;
   an antenna coupled to the microprocessor controller, whereby the microprocessor controller is programmed by signals sent through the antenna; and
   a battery coupled to the microprocessor controller located adjacent to the top surface of the flexible body.

2. The system of claim 1, wherein the drug reservoir comprises a gel pad.

3. The system of claim 1, wherein the drug reservoir comprises a membrane.

4. The system of claim 2, wherein the charged drug molecules are carried within the gel pad.

5. The system of claim 3, wherein the charged drug molecules are carried within the membrane.

6. The system of claim 1, wherein the circuitry includes flexible printed wires.

7. The drug delivery system of claim 6, wherein the flexible printed wires are made of silver or silver chloride.

8. The drug delivery system of claim 1, wherein the electroconductive material in the at least one through hole includes conductive cement.

9. An iontophoretic drug delivery system for driving charged drug molecules into a tissue, comprising:
   a flexible body configured to conform to a portion of a patient's body that includes the tissue, the flexible body including a top surface, a bottom surface, and at least one through hole;
   a drug reservoir that holds the charged drug molecules;
   an iontophoretic electrode configured to iontophoretically deliver the charged drug molecules from the drug reservoir into the tissue, the electrode being formed of an electroconductive material printed on the bottom surface of the flexible body, wherein the drug reservoir is located adjacent to the iontophoretic electrode such that the iontophoretic electrode is between the drug reservoir and the flexible body;
   a microprocessor controller configured to control iontophoretic delivery of the charged drug molecules from the drug reservoir into the tissue by the iontophoretic electrode, the microprocessor located adjacent to the top surface of the flexible body;
   circuitry that couples the microprocessor to the iontophoretic electrode, the circuitry being formed of flexible electroconductive material printed on the top surface of the flexible body;
   an electroconductive material in the at least one through hole that couples the circuitry to the iontophoretic electrode, wherein the electroconductive material fills the through hole such that moisture is prevented from passing from the bottom surface to the top surface via the through hole when at least a portion of the bottom surface is located adjacent to the tissue; and
   a high-tack adhesive placed around an outer edge of the bottom surface of the flexible body and a low-tack adhesive placed in a center of the bottom surface of the flexible body.

10. The system of claim 9, further comprising an antenna coupled to the microprocessor controller, whereby the microprocessor controller is programmed by signals sent through the antenna.

11. The system of claim 9, further comprising a battery coupled to the microprocessor controller.

12. The system of claim 9, wherein the drug reservoir comprises a gel pad.

13. The system of claim 9, wherein the drug reservoir comprises a membrane.

14. The system of claim 12, wherein the charged drug molecules are carried within the gel pad.

15. The system of claim 13, wherein the charged drug molecules are carried within the membrane.

16. The system of claim 9, wherein the circuitry includes flexible printed wires.

17. The drug delivery system of claim 16, wherein the flexible printed wires are made of silver or silver chloride.

18. The drug delivery system of claim 9, wherein the electroconductive material in the at least one through hole includes conductive cement.

19. The drug delivery system of claim 9, further comprising a moisture sensor that detects a level of moisture at an interface between the system and the patient's skin.

20. An iontophoretic drug delivery system for driving charged drug molecules into a tissue, comprising:
- a flexible body configured to conform to a portion of a patient's body that includes the tissue, the flexible body including a top surface, a bottom surface, and at least one through hole;
- a drug reservoir that holds the charged drug molecule;
- a tissue permeation enhancer that enhances permeation of the drug molecule into the tissue;
- an iontophoretic electrode configured to iontophoretically deliver the charged drug molecule from the drug reservoir into the tissue, the electrode being formed of an electroconductive material printed on the bottom surface of the flexible body, wherein the drug reservoir is located adjacent to the iontophoretic electrode such that the iontophoretic electrode is between the drug reservoir and the flexible body;
- a microprocessor controller configured to control iontophoretic delivery of the charged drug molecules from the drug reservoir into the tissue by the iontophoretic electrode, the microprocessor located adjacent to the top surface of the flexible body;
- circuitry that couples the microprocessor to the electrode, the circuitry being formed of flexible electroconductive material printed on the top surface of the flexible body;
- an electroconductive material in the at least one through hole that couples the circuitry to the iontophoretic electrode, wherein the electroconductive material fills the through hole such that moisture is prevented from passing from the bottom surface to the top surface via the through hole when at least a portion of the bottom surface is located adjacent to the tissue; and
- a battery coupled to the microprocessor controller located adjacent to the top surface of the flexible body.

21. A drug delivery system according to claim 20, wherein the permeation enhancer is in the drug reservoir.

22. A drug delivery system according to claim 21, wherein the permeation enhancer is an excipient.

23. The drug delivery system of claim 1, wherein the antenna is formed of flexible electroconductive material printed on the flexible body.

24. The drug delivery system of claim 1, wherein the flexible body includes a single flexible layer.

25. An iontophoretic drug delivery system for driving charged drug molecules into a tissue, comprising:
- a flexible body configured to conform to a portion of a patient's body that includes the tissue, the flexible body including a top surface, a bottom surface, and at least one through hole;
- a drug reservoir holding the charged drug molecules;
- an iontophoretic electrode configured to iontophoretically deliver the charged drug molecules from the drug reservoir into the tissue, the electrode being formed of an electroconductive material printed on the bottom surface of the flexible body, wherein the drug reservoir is located adjacent to the iontophoretic electrode such that the iontophoretic electrode is between the drug reservoir and the flexible body;
- a battery located adjacent to the top surface of the flexible body;
- circuitry that couples the iontophoretic electrode to the battery, the circuitry being formed of flexible electroconductive material printed on the top surface of the flexible body; and
- an electroconductive material in the at least one through hole that couples the circuitry to the iontophoretic electrode, wherein the electroconductive material fills the through hole such that moisture is prevented from passing from the bottom surface to the top surface via the through hole when at least a portion of the bottom surface is located adjacent to the tissue.

26. The drug delivery system of claim 25, wherein the iontophoretic electrode is electrically coupled to the electroconductive material via a length of wiring printed on the bottom surface of the flexible body.

* * * * *